United States Patent [19]

Gilbert

[11] 4,221,745
[45] Sep. 9, 1980

[54] PREPARATION OF HEXANITROSTILBENE

[75] Inventor: Everett E. Gilbert, Morristown, N.J.

[73] Assignee: The United States of America as represented by the Secretary of the Army, Washington, D.C.

[21] Appl. No.: 20,881

[22] Filed: Mar. 15, 1979

[51] Int. Cl.³ ............................................. C07C 79/10
[52] U.S. Cl. .................................................... 568/931
[58] Field of Search ......................... 149/105; 260/645

[56] References Cited

U.S. PATENT DOCUMENTS

| | | | |
|---|---|---|---|
| 3,699,176 | 10/1972 | Syrop | 260/645 |
| 4,085,152 | 4/1978 | Salter et al. | 260/645 |

*Primary Examiner*—Leland A. Sebastian
*Attorney, Agent, or Firm*—Nathan Edelberg; Robert P. Gibson; A. Victor Erkkila

[57] ABSTRACT

There is disclosed a process for converting 2,2', 4,4', 6,6'-hexanitrobibenzyl (HNBB) to 2,2', 4,4', 6,6'-hexanitrostilbene (HNS) by reacting HNBB with a copper ammino compound in a solvent. The HNS product can be produced in yields of greater than 65%.

10 Claims, No Drawings

PREPARATION OF HEXANITROSTILBENE

GOVERNMENT RIGHTS

The invention described herein may be manufactured, used and licensed by the Government for Governmental purposes without the payment to me of any royalties thereon.

BACKGROUND OF THE INVENTION 2,2', 4,4', 6,6'-hexanitrostilbene (HNS) is a thermally-stable explosive. It is also especially useful as a crystal modifying additive in melt-cast 2,4,6 trinitrotoluene (TNT) as disclosed in U.S. Pat. No. 3,620,857.

HNS has been prepared by oxidation of TNT. However, the process has not been entirely satisfactory since the yields based on the starting material, TNT, have been uneconomically low.

Thus, HNS can be prepared according to the process disclosed in U.S. Pat. No. 3,505,413 by the action of sodium hypochlorite on TNT at 15° C. in tetrahydrofuran/methanol solution. The yield of HNS obtained by this method is typically about 30–35% after acetone washing to remove the bulk of coprecipitated impurities, chiefly dipicryl ethane, also known as 2,2', 4,4', 6,6'-hexanitrobibenzyl (HNBB). In addition, the crude HNS produced in about 40–45% yield contains large amounts of an impurity, the so-called "red oil," believed to consist chiefly of trinitrobenzyl chloride, trinitrobenzaldehyde, trinitrobenzylalcohol, trinitrobenzoic acid, and trinitrobenzene, which causes difficulty in separating the HNS product and reuse of the tetrahydrofuran product.

This process is also described in Shipp et al, J. Org. Chem. 31, 857 (1966).

In an effort to improve yields, Salter et al, British Pat. Application No. 76/2501, Jan. 22, 1976, U.S. Pat. No. 4,085,152, treated TNT in tetrahydrofuran/methanol with aqueous sodium hypochlorite at a temperature of about 10°–20° C., then added an aqueous solution of an organic amine, preferably trimethylamine. The yields of HNS produced by this process are about 50%.

Kompolthy et al, Hungarian Pat. T/9639 No. VE-719 (CO6 f 9/04) developed a new procedure based on the air oxidation of TNT. They also observed that the preparation of HNS from TNT could be done in two steps as follows:

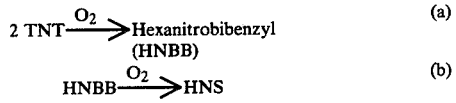

$$2 \text{ TNT} \xrightarrow{O_2} \text{Hexanitrobibenzyl} \quad (a)$$
$$\text{(HNBB)}$$
$$\text{HNBB} \xrightarrow{O_2} \text{HNS} \quad (b)$$

Shipp and Kaplan, Heat Resistant Explosives XVI, NOLTR 64-63, (1964) showed that TNT could be converted to HNBB or HNS using sodium hypochlorite under varied conditions, but they did not demonstrate any procedure for converting HNBB to HNS. Shipp and Kaplan obtained a 79% yield of HNBB from TNT.

Kompolthy et al obtained an 82% yield of HNBB and reported yields of 76–91% of HNS from HNBB using dimethylformamide or dimethylsulfoxide as solvents in a reaction mixture containing methanol, potassium hydroxide, copper sulfate and pyridine. This Kompolthy et al work has been repeated by others but yields of only 25–40% of HNS have been obtained.

There is, therefore, a need for a process for the production of HNS in high reproducible yields.

BRIEF SUMMARY OF THE INVENTION

This invention relates to the production of 2,2', 4,4', 6,6'-hexanitrostilbene (HNS) in high yields from 2,2', 4,4', 6,6'-hexanitrobibenzyl (HNBB). More particularly, this invention involves the conversion of HNBB to HNS by reacting HNBB in a suitable solvent with a copper ammino compound added per se or prepared in situ. This permits the elimination of the methanol, potassium hydroxide, and pyridine, as well as a substantial reduction in the amount of copper sulfate and solvents required in the Kompolthy et al process discussed above.

DETAILED DESCRIPTION OF THE INVENTION

The present invention is based on the discovery that HNBB can be converted to HNS in yields, based on the weight of HNBB, greater than about 65% if HNBB is reacted with a copper ammino compound with a suitable solvent.

Copper ammino compounds are well known in the art and are prepared by reacting ammonia with a salt of Cu (II). For example, copper tetraamminosulfate can be prepared from copper sulfate and ammonium hydroxide in aqueous solution. This compound can be used for converting HNBB to HNS. Another method of obtaining this compound for the conversion is to form it in situ by simply adding copper sulfate and ammonium hydroxide to the reaction mixture. This is a more preferred procedure since it is more convenient. Copper sulfate is the preferred procedure since it is more convenient. Copper sulfate is the preferred salt; other cupric salts, such as cupric chloride and cupric nitrate are also suitable for use in the process of this invention. It is much preferred to use anhydrous copper sulfate when forming the copper ammino compounds in situ. The ammino compound from copper sulfate pentahydrate is considerably less reactive in the reaction than the ammino compound from anhydrous copper sulfate. The monohydrate can be similarly used but it is not quite as good as the anhydrous copper sulfate. In addition, the anhydrous copper sulfate is substantially insoluble in the solvents, notably dimethylformamide; whereas the pentahydrate is fairly soluble. The ammino compound which is formed in situ or added directly to the reaction mixture is generally substantially insoluble in the solvents used. It should be noted that one would not expect such an insoluble material to effect a conversion of HNBB to HNS.

When forming the ammino compounds in situ, the ammonia is conveniently added as a 30% aqueous solution. This is not necessary or critical to the process of the invention, since other concentrations of ammonium hydroxide can be used, as well as anhydrous ammonia.

The solvents used are those in which the HNBB is soluble, but in which the copper ammino compounds are generally substantially insoluble. Typical solvents which are suitable and give similar results are hexamethylphosphoramide, N, N-dimethylacetamide, N-methylpyrrolidinone, and dimethylformamide. The solvent which is preferred for use in this process is dimethylformamide since it is the most readily available and least costly. The use of dimethylsulfoxide solvent results in lower yields of HNS and, although suitable, is less preferred. The following are solvents which appear to be unsatisfactory, since no yields were obtained using these solvents: acetone, tetrahydrofuran, ethyleneglycol, formamide, acetonitrile, and sulfolane.

The present process can be carried out at temperatures ranging from about room temperature (20° C.) to about 100° C., although it is not limited thereto. The reaction times and temperatures are important since each reaction mixture with the different and various amounts of starting material, solvent and copper sulfate with ammonia or copper ammino compounds requires a different time and temperature. Thus, for example, when 1.2 g. HNBB, 5 ml. DMF, 0.6 g. anhydrous copper sulfate and 0.1 g. of 30% ammonium hydroxide are reacted for four hours at 25°–30° C., the yield of HNS was 79%. When the time was reduced to one hour, the yield went down to 21%, and at two hours the yield was 46%. The time of reaction at three hours gave a satisfactory yield of 75%. Therefore, each reaction mixture has to be reacted for a time and at a temperature which would result in the highest yields. Thus, times of from one hour at 50° C. up to four hours at 25°–30° C. are required to obtain the maximum yields.

The relative amounts of reagents is also significant. For example, in the reaction mixture just discussed, if the anhydrous copper sulfate is reduced to 0.5 g, the yields after three hours at 25°–30° C. would be only 50% rather than 75%; therefore, under these conditions, 6.0 g. anhydrous copper sulfate is required to convert 1.2 g. HNBB to the good yields of HNS.

The following examples illustrate the invention.

EXAMPLE I 1.2 g. HNBB, 15 ml. DMF, 2.0 g. of finely ground copper tetraamminosulfate were mixed and heated with stirring for one hour at 50° C. The reaction mixture was poured into water and acidified with hydrochloric acid. The resulting solid was filtered and dried to give a crude product weighing 1.1 g. The crude product was purified by extraction with acetone. 0.8 g. of HNS, mp 306° C., was thus obtained, corresponding to a yield of 67% based on the HNBB employed.

EXAMPLE II 1.2 g. HNBB, 15 ml. DMF, 0.7 g. anhydrous copper sulfate, and 2 drops-0.1 g. of 30% aqueous ammonium hydroxide were mixed and stirred for one hour at 50° C. The product was recovered and purified as in Example I to give 0.9 g. of HNS, corresponding to a yield of 75%.

EXAMPLE II 1.2 g. HNBB, 5 ml. DMF, 0.6 g. anhydrous copper sulfate, and 2 drops-0.1 g. of 30% aqueous ammonium hydroxide were mixed and stirred four hours at 25°–30° C. The product was recovered and purified as in Example I. HNS of mp 310° C. was thus obtained in 79% yield. Identical experiments using shorter reaction times gave the following yields: one hour, 21%; two hours, 46%; three hours, 75%. When the experiment was run for three hours at 25°–30° C. using 0.5 g. copper sulfate instead of 0.6 g. copper sulfate, the HNS was obtained in 50% yield. Further, when the amount of DMF solvent was reduced from 5 ml to 3 ml per 1.2 g. of HNBB in the foregoing experiment, the yield of HNS obtained was reduced to 33%.

EXAMPLE IV 1.2 g. HNBB, 15 ml. DMF. 2.0 g. anhydrous copper sulfate were mixed and heated one hour at 55° C. All the HNBB was recovered unreacted. This shows that it is necessary to have the ammino compound present in the reaction mixture.

EXAMPLE V 1.2 g. HNBB, 15 ml. DMF, and 0.85 g. anhydrous copper sulfate were mixed and heated for three hours at 70° C. The resulting product was recovered as in Example I to give a 33% yield of HNS. This shows that unless the ammino compound is present in the reaction mixture even at relatively extreme conditions and high amounts of copper sulfate, the conversion to HNS was unsatisfactory.

EXAMPLE VI 1.2 g. HNBB, 15 ml. DMF, and 0.85 g. anhydrous copper sulfate were mixed and heated for two hours at 100° C. The resulting product was recovered as in Example I to give a 17% yield of HNS. This example also demonstrates that unless the ammino compound is present in the reaction mixture, the yields of HNS are unsatisfactory.

I claim:

1. A process for producing 2,2', 4,4', 6,6'-hexanitrostilbene (HNS) which comprises reacting 2,2', 4,4', 6,6'-hexanitrobibenzyl (HNBB) with a copper ammino compound in a solvent.

2. The process of claim 1 wherein said solvent is selected from the group consisting of dimethylformamide, hexamethylphosphoramide, N, N-dimethylacetamide, N-methylpyrrolidinone, and dimethylsulfoxide.

3. The process of claims 1 and 2 wherein said solvent is dimethylformamide.

4. The process of claim 1 wherein the copper ammino compound is formed in the reaction mixture in situ by the addition of a copper II salt and ammonia.

5. The process of claim 4 in which said Cu II salt is selected from the group consisting of copper sulfate, copper chloride, and copper nitrate.

6. The process of claim 5 wherein said Cu II salt is anhydrous copper sulfate.

7. The process of claim 6 wherein 0.6 g. of anhydrous copper sulfate are added to the reaction mixture for every 1.2 g. of HNBB.

8. The process of claim 1 wherein the reaction time is one hour at 50° C.

9. The process of claim 6 wherein the reaction time is three to four hours at 25°–30° C.

10. The process of claim 1 wherein the reaction is carried out at a temperature within the range of about from 20° C. to 100° C.